(12) United States Patent
Faraji et al.

(10) Patent No.: US 8,391,987 B2
(45) Date of Patent: *Mar. 5, 2013

(54) IMPLANTABLE PACKAGE TO FACILITATE INSPECTION

(75) Inventors: Boozarjomehr Faraji, Valencia, CA (US); Kevin Jun Ha, Los Angeles, CA (US); Neil Hamilton Talbot, La Crescenta, CA (US); James Singleton Little, Saugus, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/360,480

(22) Filed: Jan. 27, 2012

(65) Prior Publication Data

US 2012/0136415 A1 May 31, 2012

Related U.S. Application Data

(62) Division of application No. 12/209,068, filed on Sep. 11, 2008, now Pat. No. 8,131,376.

(60) Provisional application No. 60/971,509, filed on Sep. 11, 2007.

(51) Int. Cl.
 *A61N 1/00* (2006.01)
(52) U.S. Cl. .......................................................... 607/54
(58) Field of Classification Search ..................... 607/54
 See application file for complete search history.

(56) References Cited

U.S. PATENT DOCUMENTS

| | | | |
|---|---|---|---|
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,011,993 A * | 1/2000 | Tziviskos et al. | 607/36 |
| 6,400,989 B1 | 6/2002 | Eckmiller | |
| 6,458,157 B1 | 10/2002 | Suaning | |
| 7,771,838 B1 * | 8/2010 | He et al. | 428/632 |

* cited by examiner

*Primary Examiner* — George Manuel
*Assistant Examiner* — Robert N Wieland
(74) *Attorney, Agent, or Firm* — Scott B. Dunbar (57) ABSTRACT

The present invention is a non-destructive method of inspecting a bond, particularly a braze bond, in a hermetic package. The invention involves a unique hermetic package design adapted for ultrasonic inspection and a method of inspecting the package. This package and non-destructive inspection process are particularly useful in implantable neural stimulators such as visual prostheses.

10 Claims, 7 Drawing Sheets

IMPLANTABLE PACKAGE TO FACILITATE INSPECTION

CROSS-REFERENCE TO RELATED APPLICATIONS

This application is a divisional application of U.S. patent application Ser. No. 12/209,068, filed Sep. 11, 2008, now U.S. Pat. No. 8,131,376 for Method of Inspection of Materials for Defects, which claims benefit of U.S. Provisional Patent application Ser. No. 60/971,509, filed on Sep. 11, 2007, entitled Method for Inspection of Materials for Defects, the disclosures of which is incorporated herein by reference.

GOVERNMENT RIGHTS NOTICE

This invention was made with government support under grant No. R24EY12893-01, awarded by the National Institutes of Health. The government has certain rights in the invention.

This application is related to but in no way dependent upon U.S. patent application Ser. No. 11/385,314, filed Mar. 20, 2006, for "Package for an implantable Neural Stimulation Device".

FIELD OF THE INVENTION

The present invention is generally directed to the design and manufacture of hermetic packages, and in particular to inspection of those hermetic packages to avoid defects. Hermetic packages are particularly useful of implantable neural stimulators such as a visual prosthesis.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photo-sensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

US Patent Application 2003/0109903 to Berrang describes a Low profile subcutaneous enclosure, in particular and metal over ceramic hermetic package for implantation under the skin.

SUMMARY OF THE INVENTION

The present invention is a non-destructive method of inspecting a bond, particularly a braze bond, in a hermetic package. The invention involves a unique hermetic package design adapted for ultrasonic inspection and a method of inspecting the package. This package and non-destructive inspection process are particularly useful in implantable neural stimulators such as visual prostheses.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention is an improved hermetic package for implanting electronics within a body. Electronics are commonly implanted in the body for neural stimulation and other purposes. The improved package allows for miniaturization of the package which is particularly useful in a retinal or other visual prosthesis for electrical stimulation of the retina.

Braze materials can have varying degrees of wetting of a ceramic material. This can leave voids in braze joints. There is a need for an inspection method which can detect those voids. It has been surprisingly and unexpectedly shown that the use ultrasonic inspection including acoustic micro imaging (AMI) and scanning acoustic microscopy (SAM) is very useful for 100% success in inspection of braze joints.

Ultrasonic inspection allows a 100 percent inspection of braze joints because ultrasonic inspection is not destructive. No further verification of braze runs is required with this method. Therefore, a high increase of the reliability of the device is achieved.

The use of Acoustic Micro Imaging (AMI) can be employed as a critical nondestructive inspection technique when inspecting hermetic packages for defects and structural information. AMI works by sending very high frequency sounds (MHz range ultrasound) into the sample. An observation is made of how the sound interacts with the sample. The significant interaction occurs when a gas or vacuum space is encountered. In this case, all of the ultrasound is reflected from the interface. This makes AMI an extremely sensitive technique for finding defects in the material like delaminations, cracks and voids. Even air gap thicknesses below 250 Angstroms are highly detectable using AMI. This makes AMI more sensitive than any other technique for detecting air space type defects.

AMI is also sensitive to general material changes. Every material can be characterized by a property called acoustic impedance. When a sound passes from one material to another (such as at an interface) some or all of the energy is reflected at the boundary. The amount of ultrasound reflected is determined by the difference in the acoustic impedances. The more different the materials are the more sound is reflected. This allows for characterizing material change at a boundary.

AMI makes finer analysis of bond quality changes possible based on subtle reflection variations. In most cases, however, delaminations and voids are the most critical since they have an immediate effect on bond quality.

AMI is particularly useful for optically opaque samples because unlike light, the sound waves penetrate the materials. Metals and ceramics tend to be very good at propagating the sound, which allows the use of very high frequencies for high detail imaging. Polymers tend to be more attenuating to the ultrasound and require the use of lower frequency for better penetration.

It should be noted that human implantable devices require a high degree of reliability. Braze cracks as small as a few angstroms, will allow saline to enter the device over time and cause it to fail. Failure of an implanted device will result in expensive and possibly dangerous surgery to replace or remove the implant. It is, therefore, critical to achieve a zero failure rate in the hermeticity of an implantable device.

Figure 1:
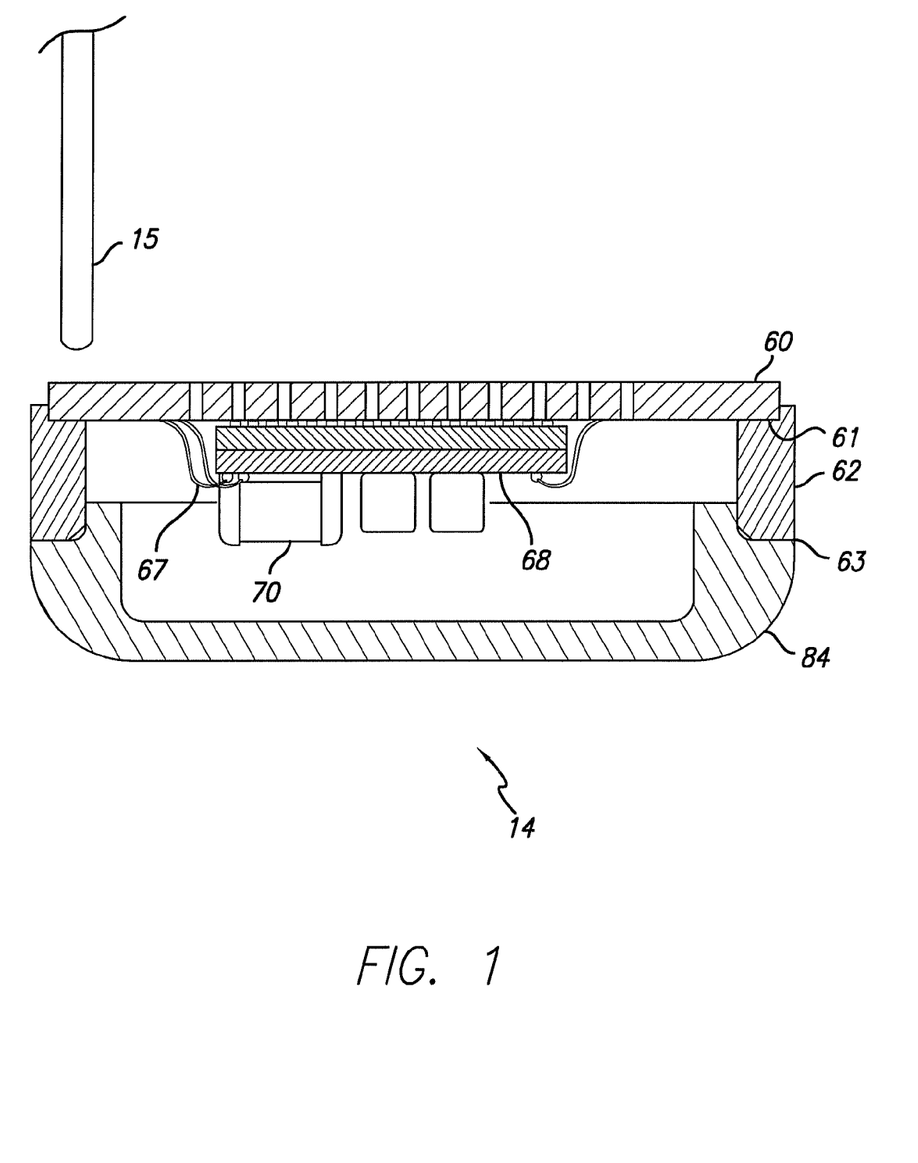
FIG. 1 is a cross-sectional view of a hermetic package adapted for inspection by acoustic energy and an acoustic transducer.

FIG. 1 shows the preferred hermetic package 14 as it is inspected. The package includes a ceramic substrate 60 brazed to a metal ring 62 by a braze joint 61. After brazing electronics, 67, 68, and 70 are attached to the ceramic substrate 60 and a mettle lid 84 is laser welded to the metal right 62 at weld joint 63. The braze joint 61 can be inspected by passing the ultrasound transducer 5 over the ceramic substrate 60 above the braze joint 61. It is important that the braze joint 61 is parallel and proximate to the surface of the ceramic substrate 60 where the ultrasonic transducer 5 passes over the device. Preferably, the thickness of the ceramic substrate 60 is less than 500 μm to allow for inspection. Since, ultrasonic inspection is based on reflected energy the thickness under the braze joint 61 is unimportant. It should be noted that ultrasonic inspection can be done after brazing before the package is completed, on the complete package, or both. Early inspection avoids the cost of completing a defective package and late inspection identifies potential damage occurring late in the process.

Figure 2:
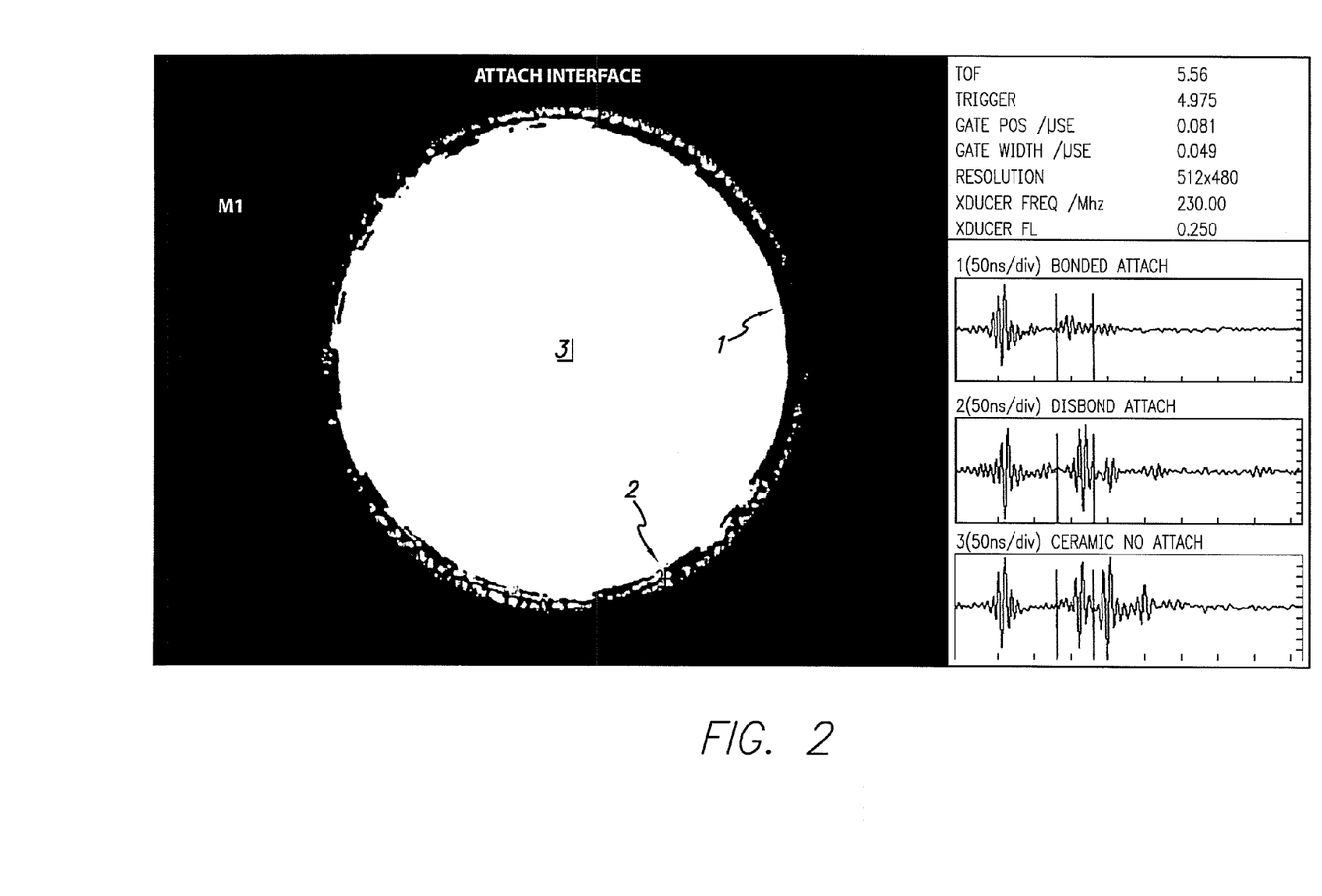
FIG. 2 is an image and graph showing reflected acoustic energy from the preferred hermetic package and how that reflected acoustic energy shows defects.

FIG. 2 shows an AMI image of the bond in the preferred package. The white circle shows the surface of a ceramic substrate. The edge of the circle shows the image of the bond. Where it appears solid black (1) the measurement of a good bond is shown. On the right side the spectra of the measurements are shown. The top spectrum [1] corresponds to the good bond (1). This can be recognized by the low amplitudes. The second spectrum [2] shows the measurement of a place with insufficient bond (2). This place (2) can be recognized in the AMI as being spattered with white spots and the second spectrum [2] shows high amplitude compared with the first spectrum. The third spectrum [3] shows the measurement of the ceramic surface (3). Since there is no bond high amplitudes are produced in the spectrum.

FIGS. 3 to 10 show the preferred application of the inventive hermetic package, as a retinal prosthesis. While described in the context of a retinal prosthesis, it should be obvious to one of skill in the art that the present invention is applicable to any hermetic package where high reliability is critical. In particular, human implantable devices such as visual prostheses, cochlear prostheses, deep brain stimulators, pacemakers, etc. are good applications for the present invention.

Figure 3:
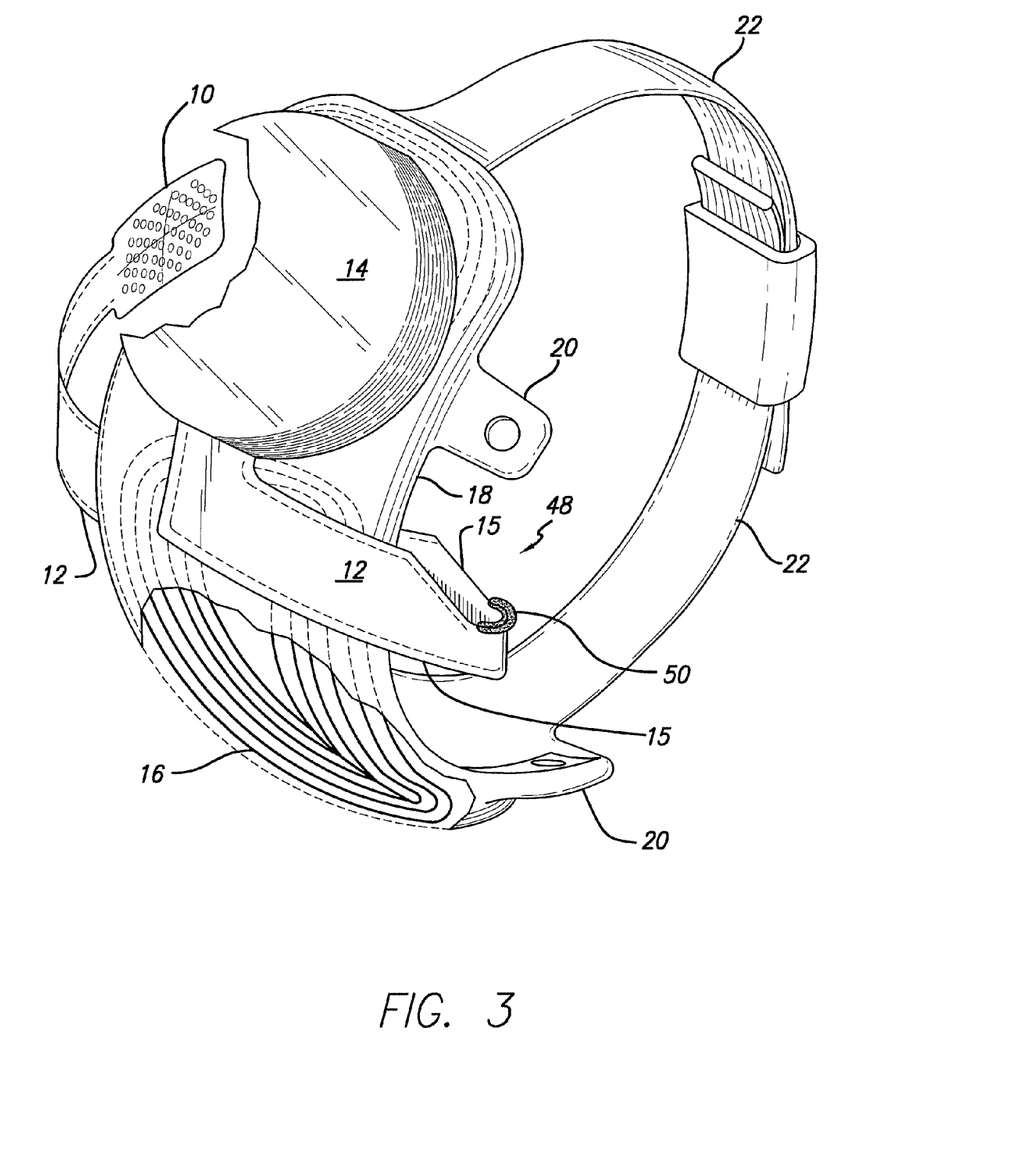
FIG. 3 is a perspective view of the implanted portion of the preferred retinal prosthesis.

FIG. 3 is a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera in the pars plana region, and is electrically coupled to an electronics package 14, external to the sclera. Further an electrode array fan tail 15 is formed of molded silicone and attaches the electrode array cable 12 to a molded body 18 to reduce possible damage from any stresses applied during implantation.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by the molded body 18. The molded body 18 holds the electronics package 14 and secondary inductive coil 16 end to end. This is beneficial as it reduces the height the entire device rises above the sclera. The design of the electronic package (described below) along with a molded body 18 which holds the secondary inductive coil 16 and electronics package 14 in the end to end orientation minimizes the thickness or height above the sclera of the entire device. This is important to minimize any obstruction of natural eye movement.

The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped secondary inductive coil 16.

Further it is advantageous to provide a sleeve or coating 50 that promotes healing of the sclerotomy. Polymers such as polyimide, which may be used to form the flexible circuit cable 12 and flexible circuit electrode array 10, are generally very smooth and do not promote a good bond between the flexible circuit cable 12 and scleral tissue. A sleeve or coating of polyester, collagen, silicone, Gore-tex or similar material would bond with scleral tissue and promote healing. In particular, a porous material will allow scleral tissue to grow into the pores promoting a good bond.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 4:
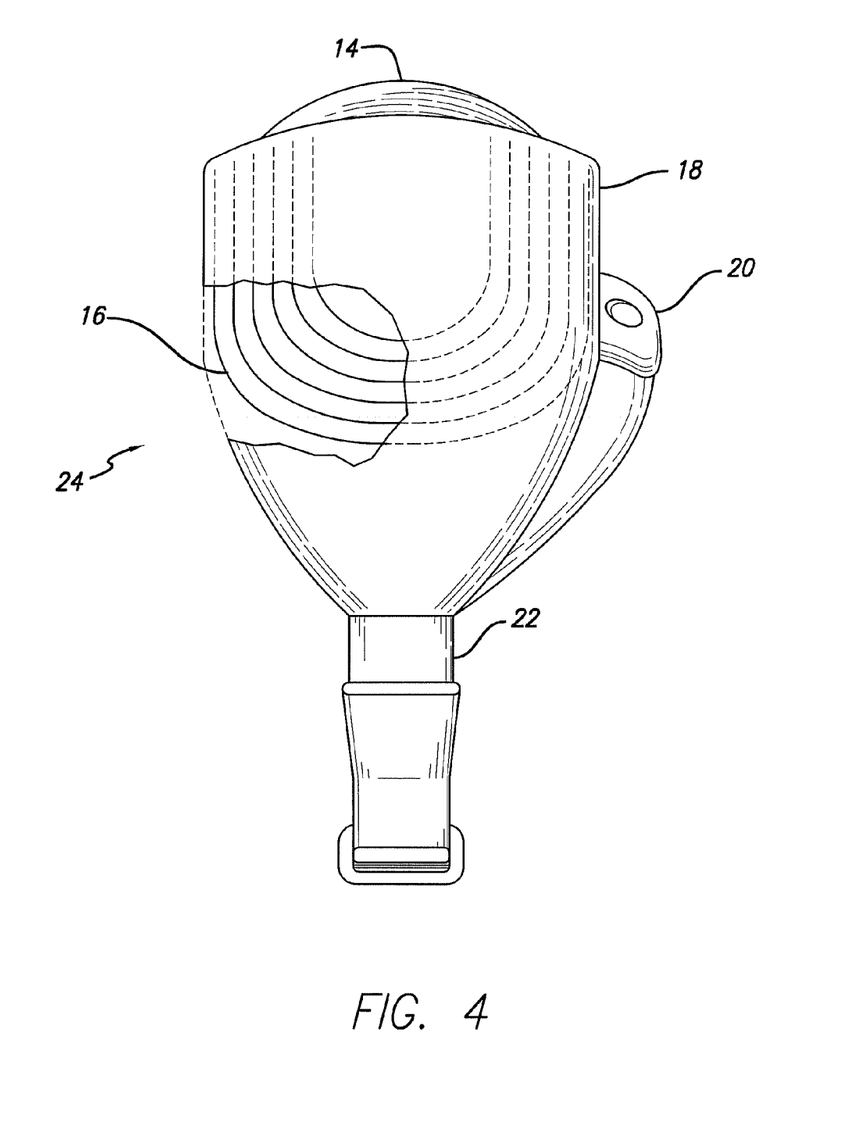
FIG. 4 is a side view of the implanted portion of the preferred retinal prosthesis showing the strap fan tail in more detail.

FIG. 4 shows a side view of the implanted portion of the retinal prosthesis, in particular, emphasizing the strap fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16 or electrode array cable 12. In order to allow the molded body 18 to slide smoothly under the lateral rectus muscle, the molded body 18 is shaped in the form of a strap fan tail 24 on the end opposite the electronics package 14.

Figure 5:
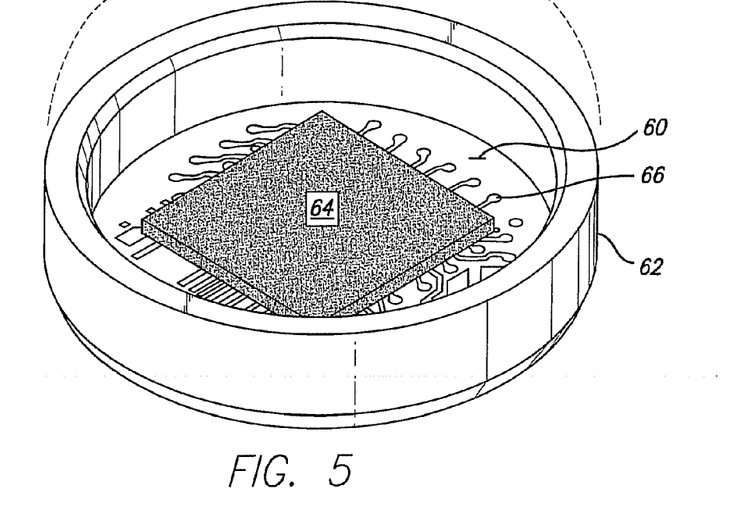
FIG. 5 is a perspective view of a partially built package showing the substrate, chip and the package wall.

Referring to FIG. 5, the hermetic electronics package 14 is composed of a ceramic substrate 60 brazed to a metal case wall 62 which is enclosed by a laser welded metal lid 84. The metal of the wall 62 and metal lid 84 may be any biocompatible metal such as, but not limited to Titanium, niobium, platinum, iridium, palladium or alloys of such metals. The ceramic substrate is preferably alumina but may include other ceramics such as Yttrium Stabilized zirconia (YSZ). The ceramic substrate 60 includes vias 65 made from biocompatible metal and a ceramic binder using thick-film techniques. The biocompatible metal and ceramic binder is preferably platinum flakes in a ceramic paste or frit which is the ceramic used to make the substrate. After the vias 65 have been filled, the substrate 60 is fired and lapped to thickness. The firing process causes the ceramic to vitrify biding the ceramic of the substrate with the ceramic of the paste forming a hermetic bond. Thin-film metallization 66 is applied to both the inside and outside surfaces of the ceramic substrate 60 and an ASIC (Application Specific Integrated Circuit) integrated circuit chip 64 is flip-chip bonded to the thin film metallization on the inside of the ceramic substrate 60.

The inside thin film metallization 66 includes a gold layer to allow electrical connection using wire bonding. The inside film metallization includes preferably two to three layers with a preferred gold top layer. The next layer to the ceramic is a titanium or tantalum or alloy thereof or other adhesion promoting metal or alloy. The next layer is preferably palladium or platinum layer or an alloy thereof. The preferred metallization includes a titanium, palladium and gold layer, but other combinations that yield acceptable adhesion and resistance to high temperature diffusion are possible. Gold is a preferred top layer because it is corrosion resistant and can be cold bonded with gold wire.

The outside thin film metallization includes a titanium adhesion layer and a platinum layer for connection to platinum electrode array traces, but other combinations that yield acceptable adhesion and resistance to high temperature diffusion are possible. for example platinum can be substituted with palladium or palladium/platinum alloy. If gold-gold wire bonding is desired a gold top layer is applied.

The package wall 62 is brazed to the ceramic substrate 60 in a vacuum furnace using a braze material in the braze joint. Preferably, the braze material is a nickel titanium or similar alloy. The braze temperature is approximately 1000° Celsius. Therefore the vias 65 and thin film metallization 66 must be selected to withstand this temperature. Also, the electronics must be installed after brazing. The chip 64 is installed inside the package using thermocompression flip-chip technology. The chip is underfilled with epoxy to avoid connection failures due to stresses caused by thermal mismatch or vibration.

Figure 6:
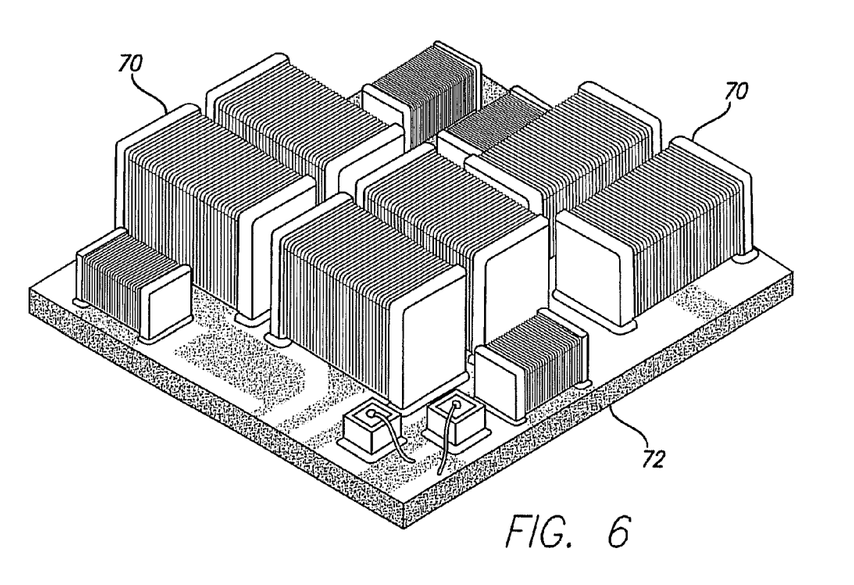
FIG. 6 is a perspective view of the hybrid stack placed on top of the chip.
Figure 7:
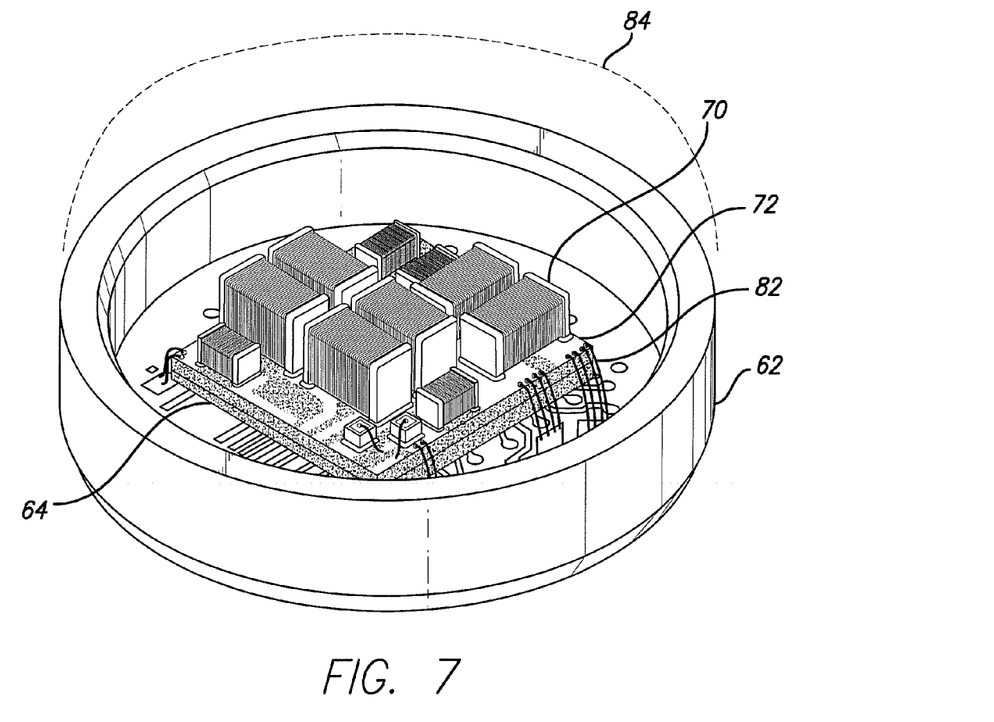
FIG. 7 is a perspective view of the partially built package showing the hybrid stack placed inside.

Referring to FIGS. 6 and 7, off-chip electrical components 70, which may include capacitors, diodes, resistors or inductors (passives), are installed on a stack substrate 72 attached to the back of the chip 64, and connections between the stack substrate 72 and ceramic substrate 60 are made using gold wire bonds 82. The stack substrate 72 is attached to the chip 64 with non-conductive epoxy, and the passives 70 are attached to the stack substrate 72 with conductive epoxy.

Figure 8:
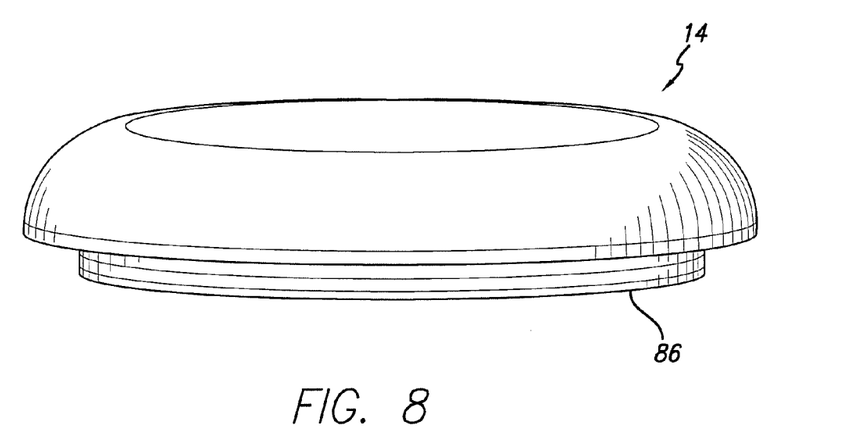
FIG. 8 is a perspective view of the lid to be welded to the top of the package.

Referring to FIG. 8, the electronics package 14 is enclosed by a metal lid 84 that, after a vacuum bake-out to remove volatiles and moisture, is attached using laser welding. A getter (moisture absorbent material) may be added after vacuum bake-out and before laser welding of the metal lid 84. The metal lid 84 further has a metal lip 86 to protect components from the welding process and further insure a good hermetic seal. The entire package is hermetically encased. Hermeticity of the vias 65, braze 61, and the entire package is verified throughout the manufacturing process. The cylindrical package was designed to have a low profile to minimize its impact on the eye when implanted.

The implant secondary inductive coil 16, which provides a means of establishing the inductive link between the external video processor (not shown) and the implanted device, preferably consists of gold wire. The wire is insulated with a layer of silicone. The secondary inductive coil 16 is oval shaped. The conductive wires are wound in defined pitches and curvature shape to satisfy both the electrical functional requirements and the surgical constraints. The secondary inductive coil 16, together with the tuning capacitors in the chip 64, forms a parallel resonant tank that is tuned at the carrier frequency to receive both power and data.

Figure 9:
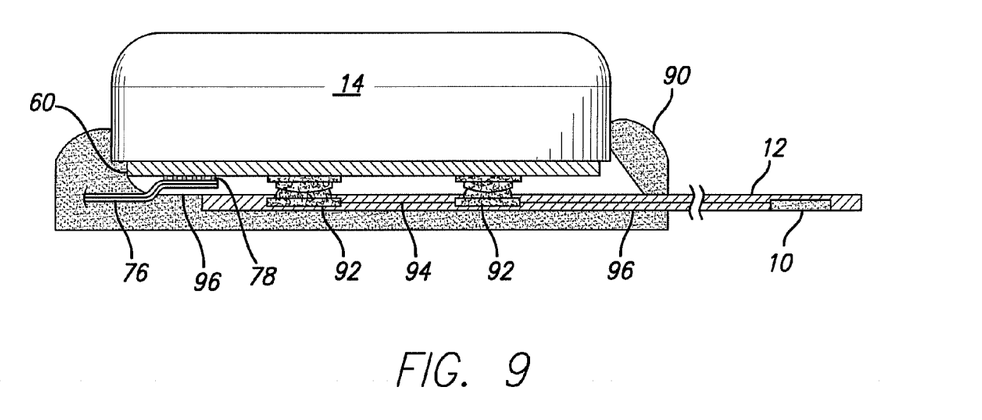
FIG. 9 is a view of the completed package attached to an electrode array.

Referring to FIG. 9, the flexible circuit 1, includes platinum conductors 94 insulated from each other and the external environment by a biocompatible dielectric polymer 96, preferably polyimide. One end of the array contains exposed electrode sites that are placed in close proximity to the retinal surface 10. The other end contains bond pads 92 that permit electrical connection to the electronics package 14. The electronic package 14 is attached to the flexible circuit 1 using a flip-chip bumping process, and epoxy underfilled. In the flip-chip bumping process, bumps containing conductive adhesive placed on bond pads 92 and bumps containing conductive adhesive placed on the electronic package 14 are aligned and cured to build a conductive connection between the bond pads 92 and the electronic package 14. Leads 76 for the secondary inductive coil 16 are attached to gold pads 78 on the ceramic substrate 60 using thermal compression or thermosonic bonding, and are then covered in epoxy. The junction of the secondary inductive coil 16, array 1, and electronic package 14 are encapsulated with a silicone overmold 90 that connects them together mechanically. When assembled, the hermetic electronics package 14 sits about 2 mm away from the end of the secondary inductive coil.

Since the implant device is implanted just under the conjunctiva it is possible to irritate or even erode through the conjunctiva. Eroding through the conjunctiva leaves the body open to infection. We can do several things to lessen the likelihood of conjunctiva irritation or erosion. First, it is important to keep the over all thickness of the implant to a minimum. Even though it is advantageous to mount both the electronics package 14 and the secondary inductive coil 16 on the lateral side of the sclera, the electronics package 14 is mounted higher than, but not covering, the secondary inductive coil 16. In other words the thickness of the secondary inductive coil 16 and electronics package should not be cumulative.

It is also advantageous to place protective material between the implant device and the conjunctiva. This is particularly important at the scleratomy, where the thin film electrode array cable 12 penetrates the sclera. The thin film electrode array cable 12 must penetrate the sclera through the pars plana, not the retina. The scleratomy is, therefore, the point where the device comes closest to the conjunctiva. The protective material can be provided as a flap attached to the implant device or a separate piece placed by the surgeon at the time of implantation. Further material over the scleratomy will promote healing and sealing of the scleratomy. Suitable materials include Dacron, Teflon (polytetraflouroethylene or PTFE), Goretex (ePTFE) Tutoplast (sterilized sclera), Mersilene (Polyester) or silicone.

Figure 10:
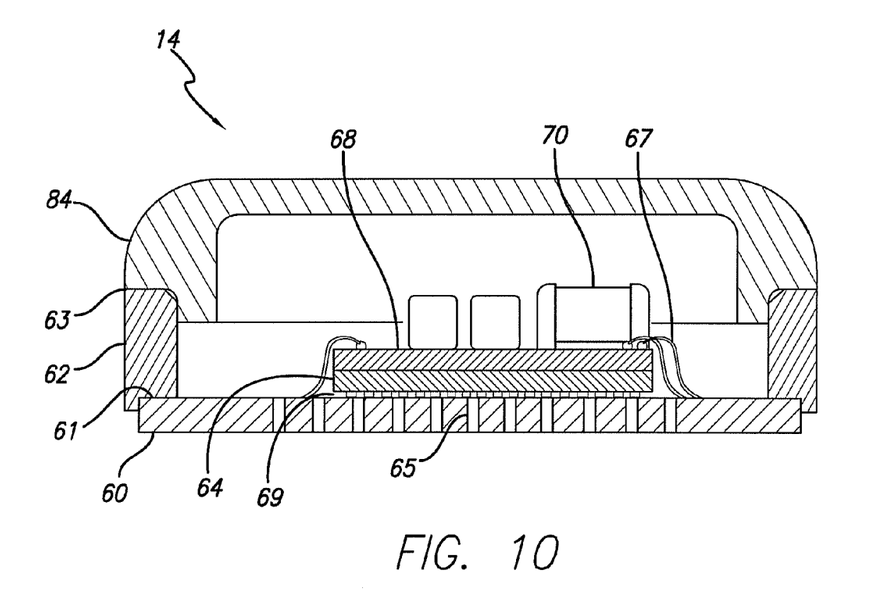
FIG. 10 is a cross-section of the package.

Referring to FIG. 10, the package 14 contains a ceramic substrate 60, with metallized vias 65 and thin-film metallization 66. The package 14 contains a metal case wall 62 which is connected to the ceramic substrate 60 by braze joint 61. On the ceramic substrate 60 an underfill 69 is applied. On the underfill 69 an integrated circuit chip 64 is positioned. On the integrated circuit chip 64 a ceramic hybrid substrate 68 is positioned. On the ceramic hybrid substrate 68 passives 70 are placed. Wirebonds 67 are leading from the ceramic substrate 60 to the ceramic hybrid substrate 68. A metal lid 84 is connected to the metal case wall 62 by laser welded joint 63 whereby the package 14 is sealed.

Accordingly, what has been shown is an improved method making a hermetic package for implantation in a body. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A hermetic package comprising:
a top having an edge surface;
a bottom having an outside surface and an inside surface;
a bond attaching said edge surface to said inside surface,
wherein said top, bottom and bond form a rigid, biocompatible, hermetic package suitable for implantation within a human body; and
wherein said bond is parallel to said outside surface and is less than 500 μm from said outside surface to reflect ultrasound energy and define said bond in an ultrasonic image of the hermetic package to enable inspection of said bond.

2. The hermetic package according to claim 1, wherein said bond is selected from the group consisting of a braze bond and a solder bond.

3. The hermetic package according to claim 1, wherein said top and said bottom are selected from the group consisting of a metal and a ceramic.

4. The hermetic package according to claim 1, wherein said hermetic package is biocompatible.

5. The hermetic package according to claim 4, wherein said hermetic package is suitable for implantation within a human body as a neural stimulator.

6. The hermetic package according to claim 5, wherein said hermetic package is suitable for implantation within a human body as a visual prosthesis.

7. A visual prosthesis comprising a hermetic package enclosing an electronic circuit and an array of electrodes driven by said electronic circuit suitable to stimulate visual neurons, wherein said hermetic package comprises:

a bottom having an inside surface, and an outside surface;

a top having an edge surface;

wherein said top, bottom and bond form a rigid, biocompatible, hermetic package suitable for implantation within a human body; and a bond attaching said edge surface to said inside surface, wherein said bond is parallel to said outside surface, wherein a distance between said bond and said outside surface is configured to allow for ultrasonic imaging of said bond.

8. The visual prosthesis according to claim 7, wherein said bottom has a thickness of less than 500 μm to allow for ultrasonic imaging of said bond.

9. The visual prosthesis according to claim 7, wherein said bottom has a side surface and said top has a lip in contact with said side surface.

10. The visual prosthesis according to claim 9, wherein said top comprises a lid portion and a middle portion, the lid portion having a second lip in contact with an inner surface of the middle portion.

* * * * *